（12）United States Patent
Hoelke et al.

(10) Patent No.: US 7,956,167 B2
(45) Date of Patent: Jun. 7, 2011

(54) **PURIFICATION OF COLLAGENASES FROM *CLOSTRIDIUM HISTOLYTICUM* LIQUID CULTURE**

(75) Inventors: Werner Hoelke, Penzberg (DE); Hellmut Eckstein, Weilheim (DE); Michaela Fischer, Wolfratshausen (DE); Antje Liehre, Penzberg (DE); Bernhard Suppmann, Weilheim (DE); Johann-Peter Thalhofer, Weilheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/474,488

(22) Filed: May 29, 2009

(65) Prior Publication Data

US 2011/0070622 A1    Mar. 24, 2011

(30) Foreign Application Priority Data

Jun. 2, 2008 (EP) .................................... 08010019

(51) Int. Cl.
*A23J 1/00* (2006.01)
(52) U.S. Cl. ............ 530/412; 435/23; 435/219; 435/220
(58) Field of Classification Search .................. 530/412; 435/23, 219, 220
See application file for complete search history.

(56) References Cited

U.S. PATENT DOCUMENTS 5,753,485 A * 5/1998 Dwulet et al. ............... 435/220

FOREIGN PATENT DOCUMENTS

| EP | 0468411 B1 | 11/1995 |
|---|---|---|
| WO | 98/22574 A2 | 5/1995 |
| WO | 03/004628 A2 | 1/2003 |

OTHER PUBLICATIONS

Antonioli, B. et al., "Characterization of Collagenase Blend Enzymes for Human Islet Transplantation," Tranplantation 84:12 (Dec. 27, 2007) 1568-1575.
Barnett, M. et al., "Quantitative Assessment of Collagenase Blends for Human Islet Isolation," Transplantation 80:6 (Sep. 27, 2005) 723-728.
Bond, M. et al., "Characterization of the Individual Collagenases from *Clostridium histolyticum*," Biochemistry 23 (1984) 3085-3091.
Bond, M. et al., "Purification and Separation of Individual Collagenases of *Clostridium histolyticum* Using Red Dye Ligand Chromatography," Biochemistry 3 (1984) 3077-3085.
Bucher, P. et al., "Assessment of a Novel Two-Component Enzyme Preparation for Human Islet Isolation and Transplantation," Transplantation 79:1 (Jan. 15, 2005) 91-97.

* cited by examiner

*Primary Examiner* — Tekchand Saidha

(57) ABSTRACT

The present invention provides a method for purifying *Clostridium histolyticum* collagenase type I and type II proteins from a complex mixture by subsequently performing a precipitation with ammonium sulfate, hydrophobic interaction chromatography, cation exchange chromatography, and anion chromatography. Conditions are provided which lead to a stabilized, partially purified preparation even after the precipitation step. The method of the invention leads to a quick and efficient removal of other proteolytic activities. The preparations according to the invention provide exceptionally pure and intact collagenase type I and type II proteins which are enzymatically active. The invention also provides blends of the two isolated proteins. The invention further provides the use of the purified collagenase proteins or blends thereof for treating a tissue sample in vitro.

11 Claims, 5 Drawing Sheets

PURIFICATION OF COLLAGENASES FROM *CLOSTRIDIUM HISTOLYTICUM* LIQUID CULTURE

RELATED APPLICATIONS

This application claims priority to EP 08010019.1 filed Jun. 2, 2008.

FIELD OF THE INVENTION

The present invention is in the field of protein biochemistry and deals with methods to provide purified *C. histolyticum* collagenase I and II enzymes. A particular technical advantage of the invention is the improvement in the rapid separation of the desired enzymes from concomitant proteolytic activities, particularly the clostripain protease. Upon purification according to the present invention the collagenases are particularly suited as ingredients in protease blends for tissue dissociation.

The present invention provides a method for purifying *Clostridium histolyticum* collagenase type I and type II proteins from a complex mixture by subsequently performing precipitation with ammonium sulfate, hydrophobic interaction chromatography, and anion chromatography. Conditions are provided which lead to a stabilized partially purified preparation even after the precipitation step. The method of the invention leads to a quick and efficient removal of other proteolytic activities. The preparations according to the invention provide exceptionally pure and intact collagenase type I and type II proteins which are enzymatically active. The invention also provides blends of the two isolated proteins. The invention further provides the use of the purified collagenase proteins or blends thereof for treating a tissue sample in vitro.

BACKGROUND OF THE INVENTION

Microbial collagenases (EC 3.4.24.3) are metalloproteinases which degrade helical regions of native collagen to small fragments. Preferred cleavage is -Gly in the sequence -Pro-Xaa-Gly-Pro-. Six main forms grouped in two classes have been isolated from *Clostridium histolyticum* that are immunologically cross-reactive but possess different sequences and different specificities. Other variants have been isolated from *Bacillus cereus, Empedobacter collagenolyticum, Pseudomonas marinoglutinosa*, and species of *Vibrio* and *Streptomyces*.

Collagenases have a role in destroying extracellular structures in the pathogenesis of bacteria such as *Clostridium histolyticum*. Thus, they are exotoxins and act as virulence factors, e.g., by facilitating the spread of gas gangrene. Collagenases normally target the connective tissue in muscle cells and other body organs. Owing to the potent hydrolytic activity toward connective tissue, collagenases and other proteinases such as thermolysin are used for tissue dissociation in vitro.

The collagenases produced by *Clostridium histolyticum* were the first collagenases to be discovered and characterized. The culture filtrate of *Clostridium histolyticum* contains a mixture of collagenases and other proteinases. Six main collagenases with molecular masses ranging from 68 to 130 kDa have been purified to homogeneity and have been designated as type I and type II collagenases (both classes of proteins are herein also referred to collectively as the "collagenase proteins"). Said clostridial collagenases contained approximately one of zinc per protein chain, whereby the zinc atom appears to be essential for enzymatic activity.

At a technical scale, clostridial collagenases are isolated from the culture filtrate of *Clostridium histolyticum*. The crude preparations contain the collagenases as well as a brown pigment, clostripain (clostridiopeptidase B), an aminopeptidase and several neutral proteinases. Crude preparations can serve as a source for the purification of the individual type I and II collagenases, but the purification scheme is quite long.

The presence of the cysteine protease clostripain in the mixture poses a significant technical problem since this peptidase progressively hydrolyzes the collagenases. In this regard collagenase of the type I appears to be more sensitive to proteolytic attack by clostripain than type II collagenase. When purifying collagenases from *C. histolyticum* culture filtrate or liquid culture supernatant it is therefore desirable to separate clostripain at an early step to minimize losses.

Bond, M., D., Van Wart, H., E., (Biochemistry 23 (1984) 3077-3085) disclose a chromatography-based purification scheme which starts with a crude enzyme preparation. In the first step the crude enzyme was chromatographed over hydroxylapatite. The mechanism of hydroxylapatite chromatography is also known as "mixed-mode" ion exchange. It involves nonspecific interactions between positively charged calcium ions and negatively charged phosphate ions on the stationary phase hydroxylapatite resin with protein negatively charged carboxyl groups and positively charged amino groups. For elution, a buffer with increasing phosphate concentration is typically used. According to Bond, M., D., Van Wart, H., E. (supra) three fractions were eluted with a potassium phosphate gradient. The first fraction contained the majority of the pigment and the third fraction contained 95% of collagenase activity. The third fraction was further subjected to gel filtration chromatography on a SEPHACRYL S200 column (GE Healthcare Bio-Sciences AB), followed by affinity chromatography over L-arginine-AFFI-GEL 202 (Bio-Rad Laboratories, Inc.). These steps combined and in the order as disclosed served to remove the brown pigment and the majority of the contaminating proteinases active against casein, benzoyl-L-arginine ethyl ester, and elastin. Reactive Red 120 dye ligand chromatography subdivided the type I and type II collagenases.

WO 2003/004628 discloses a purification scheme in which *C. histolyticum* culture supernatant is subsequently chromatographed over (1) hydroxylapatite, (2) an anion exchanger resin, and (3) a cation exchanger resin. The third fraction eluted from the hydroxylapatite column represented the collagenase I/II fraction but also contained clostripain. The anion exchanger was eluted to separate in two fractions collagenase I and collagenase II. However, both fractions still contained clostripain. The collagenases were separated from clostripain using the cation exchanger.

The methods described above represent different chromatographic approaches aiming to eliminate the undesired clostripain from the collagenases.

WO 2007/089851 discloses an assessment of precipitation with ammonium sulfate as a primary recovery step for the collagenase proteins from culture filtrate which contained significant amounts of other proteases such as clostripain. Accordingly, ammonium sulfate was added to the filtrate, initially at concentrations between 100 and 400 g/l and furthermore at concentrations between 400 and 520 g/l. Recovery of collagenase by precipitation was found to be significant at 400 g/l and the pellet generated using this concentration was found to be the easiest to resuspend. Furthermore, concentrations higher than 400 g/l apparently resulted in a very similar recovery with respect to the collagenase proteins.

In order to produce collagenases at a larger scale, WO 2007/089851 discloses the combination of (1) a specially chosen strain of C. histolyticum, (2) a fermentation process with growth conditions to optimize production of collagenases while aiming to reduce the production of clostripain, and (3) a purification scheme for collagenase I/II.

Both elements, the choice of the C. histolyticum strain and the liquid fermentation medium contribute to a reduction of clostripain in the raw material used for the purification process. Accordingly, it is noted that the conditions disclosed in WO 2007/089851 are such that the purification scheme is based on a raw preparation with a specific clostripain activity of between 0.7 and 5.5 U per mg total collagenase. According to the disclosure, these values also reflect the clostripain vs. Collagenase ratio in the culture supernatant since no noticeable separation of clostripain was found as an effect of ammonium sulfate precipitation. The comparably low amount of clostripain (between 0.7 and 5.5 U per mg total collagenase) appears to be an effect of the choice of peptones in the fermentation broth. Particularly, a porcine-derived peptone is used to provide this effect.

A raw preparation of collagenase containing fermentation product was obtained by way of ammonium sulfate precipitation from the fermentation broth.

The purification scheme of WO 2007/089851 starts with filtration of the liquid fermentation batch. Following addition of ammonium sulfate to the filtrate and removal of unsoluble matter, hydrophobic interaction chromatography is performed in the presence of ammonium sulfate in the liquid phase. Leupeptin, a well-known (reversible) inhibitor of clostripain and other serin and cystein proteases, was added to the eluted fractions comprising the collagenases, indicating that no complete separation of clostripain and/or other proteases was achieved. Leupeptin is removed during a later step in the purification process.

It is also noted that the final purified collagenase I and collagenase II preparations additionally contain N-terminally cleaved degradation products and for collagenase I also C-terminally cleaved degradation products.

The extensive use of leupeptin in the purification method of WO 2007/089851 indicates that even after hydrophobic interaction chromatography a significant residual amount of undesired proteolytic activity is present in the eluted fractions comprising the collagenases. Such residual proteases are particularly disadvantageous because they rapidly degrade the desired collagenases, whereby collagenase type I is a particularly sensitive target.

In contrast to the state of the art, the present invention is based on a culture filtrate or supernatant, in which the fermentation broth for C. histolyticum culture is free of any mammalian-derived component (such as a peptone) and in which the specific clostripain activity in the filtrate or supernatant is between about 10 and about 200 U per mg total collagenase, preferred between about 50 and about 200 U per mg total collagenase, more preferred between about 75 and about 200 U per mg total collagenase, even more preferred between about 100 and about 200 U per mg total collagenase.

The inventors have surprisingly found that a precipitation step with ammonium sulfate (($NH_4)_2SO_4$) prior to hydrophobic interaction chromatography allows to obtain a stabilized intermediate product comprising the desired type I and type II collagenases. Upon recovering of the precipitate and redissolving the same, hydrophobic interaction chromatography can be performed to reduce the activity of clostripain by the factor of about 100 to about 150 and the activity of trypsin by the factor of 100-400 in the resulting pooled eluate comprising the collagenases, whereby in the pooled eluate 80-95% of the combined collagenases I and II are present, as compared to the amounts present in the redissolved precipitate. As a result, after hydrophobic interaction chromatography the mixture of collagenases I and II is substantially stable in the absence of any protease inhibitor (e.g., leupeptin). That is to say, under the conditions of the invention none or only minimal proteolytic degradation of collagenase I or II is detectable. Importantly, removal of concomitant non-collagenase proteases in the preparation is so effective that further purification of collagenases I and II leads to products having an exceptional purity and even lacking N-terminal degradation.

SUMMARY OF THE INVENTION

A first aspect of the invention is a method for partially purifying Clostridium histolyticum collagenase type I and type II proteins from a complex mixture, comprising the steps of (a) providing the complex mixture dissolved in an aqueous liquid phase; (b) forming a precipitate of collagenase type I and type II proteins by dissolving ammonium sulfate in the liquid phase of step (a); (c) separating the precipitate of step (b) from the liquid phase; (d) dissolving the precipitate of step (c) in an aqueous buffer comprising Ca2+ ions and a pH between 6.0 and 8.0, and adjusting the conductivity of the buffer with the dissolved precipitate to a value of between 50 and 300 mS/cm, thereby forming a complex buffered solution comprising collagenase type I and type II proteins; (e) extracting the complex buffered solution of step (d) by contacting the same with a hydrophobic stationary phase, and adsorbing collagenase type I and type II proteins to the stationary phase; (f) separating the hydrophobic stationary phase with the adsorbed collagenase type I and type II proteins of step (e) from the extracted solution; (g) eluting the collagenase type I and type II proteins from the stationary phase of step (f); thereby purifying the collagenase type I and type II proteins. A second aspect of the invention is a preparation comprising enzymatically active Clostridium histolyticum collagenase type I and type II proteins, obtainable by the method according to the invention. A third aspect of the invention is a purified preparation of enzymatically active Clostridium histolyticum collagenase type I, obtainable by the method according to the invention. A fourth aspect of the invention is a purified preparation of enzymatically active Clostridium histolyticum collagenase type II, obtainable by the method according to the invention. A fifth, aspect of the invention is a blend comprising Clostridium histolyticum collagenase type I and Clostridium histolyticum collagenase type II, characterized in that a first measured amount of a purified preparation according to the invention is mixed with a second measured amount of a purified preparation according to the invention. A sixth aspect of the invention is the use of a purified preparation of enzymatically active Clostridium histolyticum collagenase type I according to the invention, a purified preparation of enzymatically active Clostridium histolyticum collagenase type II according to the invention or a blend according to the invention for processing a tissue sample, whereby collagen present in the sample is digested.

DETAILED DESCRIPTION OF THE INVENTION

Figure 1:
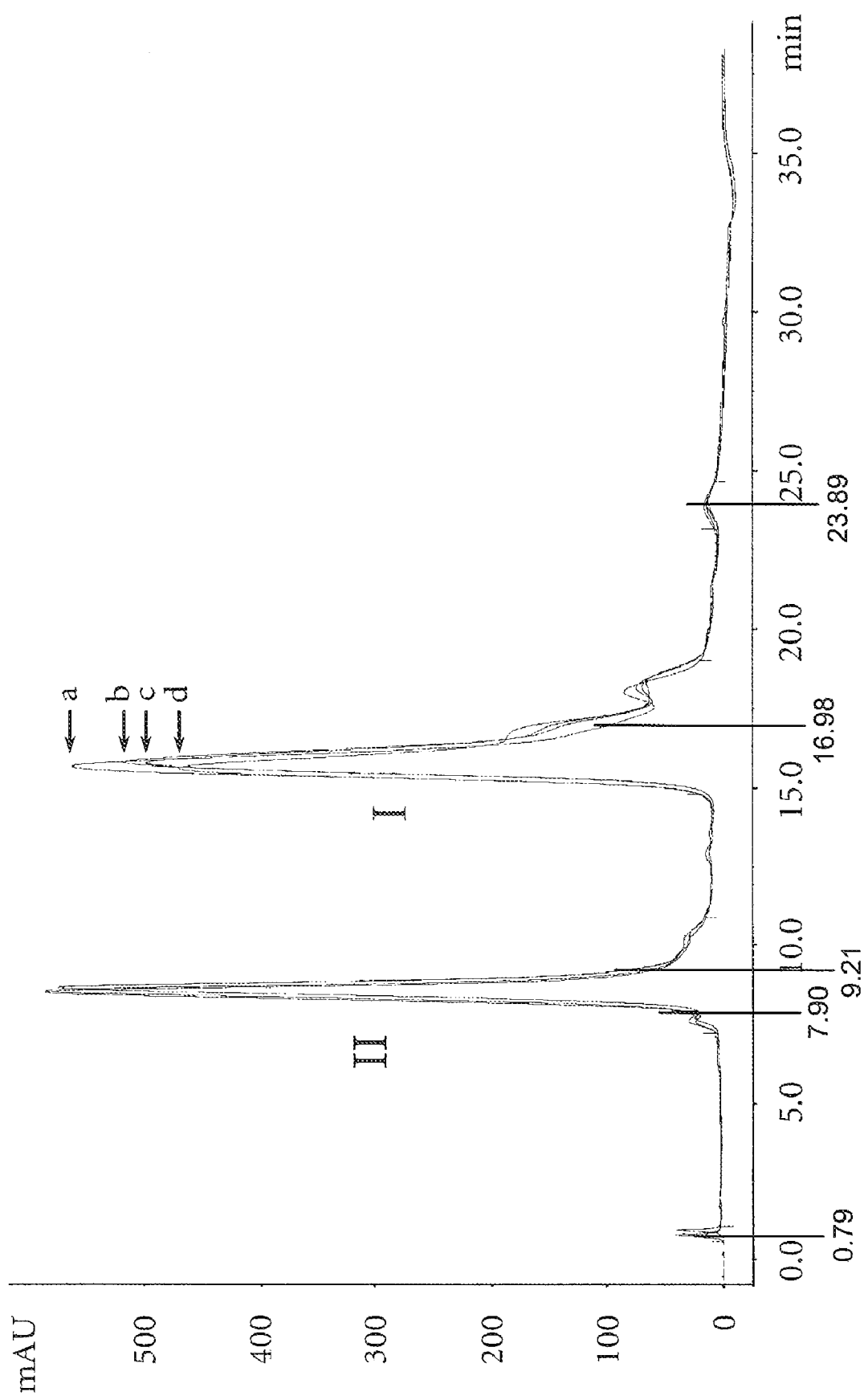
FIG. 1 Stability of collagenase type II and type I proteins after hydrophobic interaction chromatography. Mono Q analytics were performed according to Example 5. An overlay of four chromatograms is shown. The peaks designated "II" and "I" refer to the collagenase type II and type I proteins, respectively. The arrows marked "a", "b", "c", and "d" indicate the height of the main peak corresponding to the collagenase type I protein after incubation of the purified mixture at 4° C. for 0 days ("a"), 2 days ("b"), 3 days ("c"), and 6 days ("d").

Certain terms are used with particular meaning, or are defined for the first time, in this description of the present invention. For the purposes of the present invention, the terms used are defined by their art-accepted definitions, when such exist, except that when those definitions conflict or partially conflict with the definitions set forth below. In the event of a conflict in definition, the meaning of a terms is first defined by any of the definitions set forth below.

The present invention refers to the C. histolyticum collagenases (EC 3.4.24.3) of type I and type II as previously given in Bond, M., D., van Wart, H., E. Biochemistry 23 (1984), 3077-3085 and Bond, M., D. van Wart, H. E., Biochemistry 23 (1984), 3085-3091.

The term "comprising" is used in the description of the invention and in the claims to mean "including, but not necessarily limited to".

The articles "a" and "an" are used herein to refer to one or to more than one (i.e. to at least one) of the grammatical object of the article. By way of example, "a compound" means one compound or more than one compound.

When designating a range of numerical values such as a concentration range, the range is indicated by the word "between", followed by a first value n1 and a second value n2. The lower boundary of the designated range is understood as being the value equal to or higher than the first value. The higher boundary of the designated range is understood as being the value equal to or lower than the second value". Thus, a value x the designated range is given by $n1 \leq x \leq n2$.

If not stated otherwise, it is understood that the term "about" in combination with a numerical value n indicates a value x in the interval given by the numerical value ±5% of the value, i.e. $n-0.05*n \leq x \leq n+0.05*n$. In case the term "about" in combination with a numerical value n describes a preferred embodiment of the invention, the value of n is most preferred, if not indicated otherwise.

Amino acid identification uses the three-letter abbreviations as well as the single-letter alphabet of amino acids, i.e., Asp D Aspartic acid, Ile I Isoleucine, Thr T Threonine, Leu L Leucine, Ser S Serine, Tyr Y Tyrosine, Glu E Glutamic acid, Phe F Phenylalanine, Pro P Proline, His H Histidine, Gly G Glycine, Lys K Lysine, Ala A Alanine, Arg R Arginine, Cys C Cysteine, Trp W Tryptophan, Val V Valine, Gln Q Glutamine, Met M Methionine, Asn N Asparagine.

The "complex mixture" from which the collagenase proteins are purified herein comprises the proteins of interest and one or more impurities. The composition may be "partially purified" (i.e. having been subjected to one or more purification steps or may be obtained directly from a C. histolyticum culture producing the proteins (e.g., the complex mixture may comprise harvested culture fluid).

An "impurity" is a material that is different from any of the desired proteins. The impurity includes, but is not limited to, a C. histolyticum protein, a polypeptide other than any of the target proteins, nucleic acid, endotoxin, exotoxin, phage component, etc. As used herein, "protein" refers generally to polypeptides having more than about ten amino acids. Each of the collagenase I ("collagenase type I") and collagenase II ("collagenase type II") proteins including each of the respective isoforms, under the provision that the protein is characterized by a collagenase enzymatic activity, is also referred to as a "desired protein", a "target protein" or a "protein of interest". An example therefor is any one of the collagenase proteins, according to Bond, M., D., van Wart, H., E., Biochemistry 23 (1984), 3085-3091. The plural form of any one of the terms "desired protein", "target protein", "protein of interest", "collagenase enzyme" or "collagenase protein" refers to the collagenase type I and type II proteins altogether, if not explicitly stated otherwise. By "purifying" a protein from a composition comprising the protein and one or more impurities is meant increasing the degree of purity of the protein in the composition by removing (completely or partially) at least one impurity from the composition. According to the present invention, purification of the collagenase proteins is performed by a process comprising ammonium sulfate precipitation, hydrophobic interaction chromatography, and cation exchange chromatography, whereby the purification steps are performed in this particular order. A "purification step" is part of the overall purification process resulting in a "homogeneous" composition of C. histolyticum collagenase type I and type II proteins. Accordingly, when present in a homogeneous composition, a protein is "purified to homogeneity". The collagenase type I and type II proteins are purified to homogeneity by way of an additional and subsequent step of anion exchange chromatography.

The term "chromatography" refers to the process by which a solute of interest in a mixture is separated from other solutes in the mixture as a result of differences in rates at which the individual solutes of the mixture migrate through a stationary medium under the influence of a moving phase, or in bind and elute processes. A "salt" is a compound formed by the interaction of an acid and a base. A salt useful for the invention include, but are not limited to chloride (e.g., sodium chloride, calcium chloride) and sulfate (e.g., ammonium sulfate). As used herein, "solvent" refers to a liquid substance capable of dissolving or dispersing one or more other substances to provide a solution.

The term "ion-exchange" and "ion-exchange chromatography" refers to the chromatographic process in which a solute of interest (such as a protein) in a mixture interacts with a charged compound linked (such as by covalent attachment) to a solid phase ion exchange material such that the solute of interest interacts non-specifically with the charged compound more or less than solute impurities or contaminants in the mixture. One or more contaminating solutes in the mixture (impurities) elute from a column of the ion exchange material faster or slower than the solute of interest or are bound to or excluded from the resin relative to the solute of interest. "Ion-exchange chromatography" specifically includes cation exchange, anion exchange, and mixed mode chromatography. An "ion exchange material" refers to a solid phase that is negatively charged (i.e. a cation exchange resin) or positively charged (i.e. an anion exchange resin). The charge may be provided by attaching one or more charged ligands to the solid phase, e.g., by covalent linking. Alternatively, or in addition, the charge may be an inherent property of the solid phase (e.g., as is the case for silica, which has an overall negative charge).

By "solid phase" or "stationary phase" is meant a non-aqueous matrix to which one or more charged ligands can adhere. The solid or stationary phase may be a purification column, a discontinuous phase of discrete particles, a membrane, or filter etc. Examples of materials for forming the solid phase include polysaccharides (such as agarose and cellulose); and other mechanically stable matrices such as silica (e.g., controlled pore glass), poly(styrenedivinyl)benzene, polyacrylamide, ceramic particles and derivatives of any of the above.

A "cation exchange resin" refers to a solid phase which is negatively charged, and which thus has free cations for exchange with cations in an aqueous solution passed over or through the solid phase. A negatively charged ligand attached to the solid phase to form the cation exchange resin may, e.g., be a carboxylate or sulfonate. Commercially available cation exchange resins include carboxy-methyl-cellulose, sulphopropyl (SP) immobilized on agarose (e.g., SP-SEPHAROSE Fast Flow or SP-SEPHAROSE High Performance) and sulphonyl immobilized on agarose (e.g., S-SEPHAROSE Fast Flow). A "mixed mode ion exchange resin" refers to a solid phase which is covalently modified with cationic, anionic, and hydrophobic moieties.

The term "anion exchange resin" is used herein to refer to a solid phase which is positively charged, e.g., having one or more positively charged ligands, such as quaternary amino groups, attached thereto. Commercially available anion exchange resins include DEAE cellulose, QAE SEPHADEX (GE Healthcare Bio-Sciences AB) and Fast Flow Q SEPHAROSE.

A "buffer" is a solution that resists changes in pH by the action of its acid-base conjugate components. Various buffers which can be employed depending, for example, on the desired pH of the buffer are described in Buffers. A Guide for the Preparation and Use of Buffers in Biological Systems, Gueffroy, D., ed. Calbiochem Corporation (1975). In one embodiment, the buffer has a pH in the range from about 2 to about 9, alternatively from about 3 to about 8, alternatively from about 4 to about 7 alternatively from about 5 to about 7. Non-limiting examples of buffers that will control the pH in this range include MES, MOPS, MOPSO, Tris, HEPES, phosphate, acetate, citrate, succinate, and ammonium buffers, as well as combinations of these.

A "loading buffer" is that which is used to load the composition comprising the polypeptide molecule of interest and one or more impurities to the ion exchange resin. The loading buffer has a conductivity and/or pH such that the polypeptide molecule of interest (and generally one or more impurities) is/are bound to the ion exchange resin or such that the protein of interest flows through the column while the impurities bind to the resin. The term "wash buffer" when used herein refers to a buffer used to wash or re-equilibrate the ion exchange resin, prior to eluting the polypeptide molecule of interest. Conveniently, the wash buffer and loading buffer may be the same, but this is not required. An "elution buffer" is used to elute the polypeptide of interest from the solid phase. The conductivity and/or pH of the elution buffer is/are such that the polypeptide of interest is eluted from the ion exchange resin. A "regeneration buffer" may be used to regenerate the ion exchange resin such that it can be re-used. The regeneration buffer has a conductivity and/or pH as required to remove substantially all impurities and the polypeptide of interest from the ion exchange resin.

The term "conductivity" refers to the ability of an aqueous solution to conduct an electric current between two electrodes. In solution, the current flows by ion transport. Therefore, with an increasing amount of ions present in the aqueous solution, the solution will have a higher conductivity. The unit of measurement for conductivity is milliSiemens (mS) per centimeter (mS/cm), and can be measured using a conductivity meter. The conductivity of a solution may be altered by changing the concentration of ions therein. For example, the concentration of a buffering agent and/or concentration of a salt (e.g., $(NH_4)_2SO_4$, NaCl or $CaCl_2$) in the solution may be altered in order to achieve the desired conductivity. Preferably, the salt concentration of the various buffers is modified to achieve the desired conductivity as in described in the Example section further below.

By "binding" a molecule to a stationary phase (such as a hydrophobic interaction material or an ion exchange material) is meant exposing the molecule to the stationary phase under appropriate conditions (pH/conductivity) such that the molecule is "adsorbed" or reversibly immobilized in or on the stationary phase. This can be effected by virtue of hydrophobic or ionic interactions between the molecule and a functional group or groups of the stationary phase. By "washing" the stationary phase is meant passing an appropriate buffer through or over the stationary phase. In a preferred embodiment of the invention the target proteins remain adsorbed to or on the stationary phase during the process of washing. To "elute" a molecule (e.g., a desired polypeptide or an impurity) from a stationary phase is meant to remove the molecule therefrom by altering a parameter selected from the group consisting of the composition, conductivity, ionic strength and pH of the buffer surrounding the stationary phase such that the molecule is released from the functional group or groups of the stationary phase.

The present invention provides methods for purifying enzymatically active collagenase proteins from *C. histolyticum* culture supernatant, filtrate or the like, i.e. a complex solution comprising collagenase type I and type II proteins as dissolved matter. In order to limit proteolytic digestion of the target proteins the complex solution is cooled to a temperature of between 2° C. and 10° C. Subsequent purification steps are performed at a temperature in this range, if not indicated otherwise.

Once the solution containing the proteins of interest is obtained, their separation from undesired components in the solution is usually attempted using a combination of different chromatography techniques. Undesired components include residual constituents of the culture medium (such as proteins, peptone, carbohydrate and other compounds) or other proteins produced by the cell (i.e. non-collagenase proteins).

In a first embodiment of the invention chromatographic purification is preceded by an ammonium sulfate precipitation step. By way of precipitation, a significant portion of undesired components is separated from the collagenase proteins. In the liquid culture supernatant, filtrate or the like (also collectively referred to as "cleared culture supernatant") a precipitate comprising the collagenase proteins is formed, in the presence of ammonium sulfate at a concentration of between 2.6 M and 2.8 M (the target concentration of $(NH_4)_2SO_4$).

Ammonium sulfate precipitation is a method of protein purification by altering solubility of protein. It is a specific case of a more general technique known as salting out. Ammonium sulfate is commonly used as its solubility is so high that salt solutions with high ionic strength are allowed. The solubility of proteins varies according to the ionic strength of the solution, and hence according to the salt concentration. Two distinct effects are observed: at low salt concentrations, the solubility of the protein increases with increasing salt concentration (i.e. increasing ionic strength), an effect termed salting in. As the salt concentration (ionic strength) is increased further, the solubility of the protein begins to decrease. At sufficiently high ionic strength, the protein will be almost completely precipitated from the solution (salting out). Since proteins differ markedly in their solubilities at high ionic strength, salting-out is a very useful procedure to assist in the purification of a given protein. The commonly used salt is ammonium sulfate, as it is very water soluble and has no adverse effects upon enzyme activity. Ammonium sulfate can be added as dry matter while continuously stirring the liquid phase. Alternatively, ammonium sulfate can be added as a concentrated solution, e.g., as a saturated aqueous solution. Preferably, $(NH_4)_2SO_4$ is added continuously over a period of about 30 min to the liquid culture supernatant, filtrate or the like, and dissolved therein, in order to reach the target concentration of $(NH_4)_2SO_4$.

After adjusting an ammonium sulfate concentration of between 2.6 M and 2.8 M the precipitate is allowed to form for a period of between about 10 min and about 30 min. The precipitated protein is then removed by centrifugation and then the ammonium sulfate concentration is increased to a value that will precipitate most of the protein of interest whilst leaving the maximum amount of protein contaminants still in solution. The precipitated protein of interest is recovered by centrifugation and dissolved in fresh buffer for the next stage of purification.

This technique is useful to quickly remove large amounts of contaminant proteins, as a first step in the purification scheme of the invention. It can also be employed during later stages of purification to concentrate protein from dilute solution following procedures such as gel filtration and other chromatographic separation techniques.

Chromatography techniques separate mixtures of proteins on the basis of their charge, degree of hydrophobicity, or size. Several different chromatography resins are available for each of these techniques, allowing accurate tailoring of the purification scheme to the particular protein involved. The essence of each of these separation methods is that proteins can be caused either to move at different rates down a long column, achieving a physical separation that increases as they pass further down the column, or to adhere selectively to the separation medium, being then differentially eluted by different solvents. In some cases, the desired protein is separated from impurities when the impurities specifically adhere to the column, and the protein of interest does not, that is, the protein of interest is present in the "flow-through."

Ion-exchange chromatography, named for the exchangeable counterion, is a procedure applicable to purification of ionizable molecules. Ionized molecules are separated on the basis of the non-specific electrostatic interaction of their charged groups with oppositely charged molecules attached to the solid phase support matrix, thereby retarding those ionized molecules that interact more strongly with solid phase. The net charge of each type of ionized molecule, and its affinity for the matrix, varies according to the number of charged groups, the charge of each group, and the nature of the molecules competing for interaction with the charged solid phase matrix. These differences result in resolution of various molecule types by ion-exchange chromatography. In typical protein purification using ion exchange chromatography, a mixture of many proteins derived from a host cell, such as in mammalian cell culture, is applied to an ion-exchange column. After non-binding molecules are washed away, conditions are adjusted, such as by changing pH, counter ion concentration and the like in step- or gradient-mode, to release from the solid phase a non-specifically retained or retarded ionized protein of interest and separating it from proteins having different charge characteristics. Anion exchange chromatography involves competition of an anionic molecule of interest with the negative counter ion for interaction with a positively charged molecule attached to the solid phase matrix at the pH and under the conditions of a particular separation process. By contrast, cation exchange chromatography involves competition of a cationic molecule of interest with the positive counter ion for a negatively charged molecule attached to the solid phase matrix at the pH and under the conditions of a particular separation process. Mixed mode ion exchange chromatography involves the use of a combination of cation and anion exchange chromatographic media in the same step. In particular, "mixed-mode" refers to a solid phase support matrix to which is covalently attached a mixture of cation exchange, anion exchange, and hydrophobic interaction moieties.

Hydrophobic interaction chromatography (also referred to as "HIC") is a separation technique which uses the properties of hydrophobicity to separate proteins from one another. In this type of chromatography, hydrophobic groups such as phenyl, octyl, or butyl, are attached to the stationary phase. Proteins that pass through the column that have hydrophobic amino acid side chains on their surfaces are able to interact with and bind to the hydrophobic groups on the column. Typically, in a HIC separation a buffer with a high ionic strength, usually ammonium sulfate, is initially applied to the column. The salt in the buffer reduces the solvation of sample solutes thus as solvation decreases, hydrophobic regions that become exposed are adsorbed by the medium. The more hydrophobic the target molecule to be adsorbed, the less salt needed to promote binding. To elute the adsorbed proteins from the stationary phase, the salt concentration is decreased in order of increasing hydrophobicity. Gradual decrease can be applied in the form of a gradient. Additionally, elution can also be achieved through the use of certain organic modifiers or the use of a detergent.

For HIC, the stationary phase is capable of forming hydrophobia interactions with other molecules. These interactions are too weak in water. However, addition of salts to the buffer result in hydrophobic interactions. Salts which increase hydrophobic interactions include (in the order of their ability to enhance interactions): $Na_2SO_4$, $K_2SO_4$, $(NH_4)_2SO_4$, NaCl, $NH_4Cl$, NaBr, and NaSCN.

Although reversed phase chromatography and hydrophobic interaction chromatography are very similar, the ligands in reversed phase chromatography typically are much more hydrophobic than the ligands in hydrophobic interaction chromatography. This enables hydrophobic interaction chromatography to the use of more moderate elution conditions, which do not disrupt the sample nearly as much. A preferred stationary phase for performing HIC includes TOYOPEARL Phenyl-650 (Tosoh Corp.), Phenyl SEPHAROSE CL-4B, Phenyl SEPHAROSE 6 Fast Flow (High Sub) and Phenyl SEPHAROSE 6 Fast Flow (Low Sub).

An important advantage provided by the present invention is an optimized partial purification which particularly separates clostripain activity from the collagenase proteins. Thus, degradation of the collagenase proteins during subsequent purification steps is minimized. In further detail, the present invention comprises the following aspects and preferred embodiments:

1. A method for purifying *Clostridium histolyticum* collagenase type I and type II proteins from a complex mixture, comprising the steps of
   (a) providing the complex mixture dissolved in an aqueous liquid phase;
   (b) forming a precipitate of collagenase type I and type II proteins by dissolving ammonium sulfate in the liquid phase of step (a);
   (c) separating the precipitate of step (b) from the liquid phase;
   (d) dissolving the precipitate of step (c) in an aqueous buffer comprising Ca2+ ions and a pH between 6.0 and 8.0, and adjusting the conductivity of the buffer with the dissolved precipitate to a value of between 50 and 300 mS/cm, thereby forming a complex buffered solution comprising collagenase type I and type II proteins;
   (e) extracting the complex buffered solution of step (d) by contacting the same with a hydrophobic stationary phase, and adsorbing collagenase type I and type II proteins to the stationary phase;
   (f) separating the hydrophobic stationary phase with the adsorbed collagenase type I and type II proteins of step (e) from the extracted solution; and
   (g) eluting the collagenase type I and type II proteins from the stationary phase of step (f);
   thereby purifying the collagenase type I and type II proteins.

2. The method according to item 1, characterized in that step (b) is performed by dissolving in the liquid phase ammonium sulfate at a concentration of between about 2.6 M and about 3.2 M, more preferred between about 2.6 M and about 2.8 M, thereby forming the precipitate comprising collagenase type I and type II proteins.

3. The method according to item 2, characterized in that between about 417 g and about 458 g of ammonium sulfate are dissolved in 1 l of liquid phase.

4. The method according to any of the items 2 and 3, characterized in that after step (c) in the dissolvable matter of the precipitate the clostripain proteolytic activity is reduced by a factor of between 90 and 150, and the tryptic activity is reduced by a factor of between 100 and about 400, relative to the respective proteolytic activities in the dissolved complex mixture of step (a).

5. The method according to item 4, characterized in that the clostripain proteolytic activity is reduced by a factor of between 100 and 150, and the tryptic activity is reduced by a factor of between about 200 and about 400.

6. The method according to item 5, characterized in that the clostripain proteolytic activity is reduced by a factor of up to 150, and the tryptic activity is reduced by a factor of up to about 400.

7. The method according to any of the items 1 to 6, characterized in that step (c) is followed by a further step (c') comprising storing the precipitate at a temperature of 10° C. or lower.

8. The method according to item 7, characterized in that the temperature of storage is between 10° C. and −20° C.

9. The method according to item 8, characterized in that the temperature of storage is −20° C.

10. The method according to any of the items 1 to 9, characterized in that in step (d) the aqueous buffer comprises $Ca^{2+}$ ions at a concentration of 5 mM.

11. The method according to any of the items 1 to 10, characterized in that in step (d) the aqueous buffer comprises a buffer compound capable of buffering in the range of pH 6 to 8.5.

12. The method according to item 11, characterized in that the buffer compound is present at a concentration of 20 mM.

13. The method according to any of the items 1 to 12, characterized in that in step (d) the aqueous buffer comprises a buffer compound selected from the group consisting of BES (N,N-Bis(2-hydroxyethyl)-2-aminoethanesulfonic acid), Tris(2-Amino-2-(hydroxymethyl)propane-1,3-diol), BisTris(Bis(2-hydroxyethyl)amino-tris(hydroxymethyl)methane), BisTris propane (1,3-bis(tris(hydroxymethyl)methylamino)propane), HEPES (N-(2-hydroxyethyl)-piperazine-N'-2-ethanesulfonic acid), MES (2-(N-morpholino)ethanesulfonic acid), MOPS (3-(N-morpholino)propanesulfonic acid), MOPSO (3-morpholino-2-hydroxypropanesulfonic acid), PIPES (piperazine-1,4-bis(2-ethanesulfonic acid)), TAPS(N-Tris (hydroxymethyl)methyl-3-aminopropanesulfonic acid), TES (N-Tris(hydroxymethyl)methyl-2-aminoethanesulfonic acid), TEA (Triethanolamine), and Tricine (N-(2-Hydroxy-1,1-bis(hydroxymethyl)ethyl)glycine).

14. The method according to item 13, characterized in that in step (d) the aqueous buffer comprises TES or HEPES.

15. The method according to any of the items 1 to 14, characterized in that in step (d) the pH of the aqueous buffer is neutral.

16. The method according to any of the items 1 to 15, characterized in that in step (d) the pH of the complex buffered solution is neutral.

17. The method according to any of the items 1 to 16, characterized in that in step (d) the conductivity of the complex buffered solution is between 50 mS/cm and 290 mS/cm.

18. The method according to item 17, characterized in that in step (d) the conductivity of the complex buffered solution is between 50 mS/cm and 200 mS/cm.

19. The method according to item 18, characterized in that in step (d) the conductivity of the complex buffered solution is between 50 mS/cm and 150 mS/cm.

20. The method according to item 19, characterized in that in step (d) the conductivity of the complex buffered solution is between 90 mS/cm and 100 mS/cm.

21. The method according to item 20, characterized in that in step (d) the conductivity of the complex buffered solution is about 95 mS/cm.

22. The method according to any of the items 17 to 21, characterized in that the concentration of ammonium sulfate in the complex buffered solution is between 0.3 M and 1 M.

23. The method according to item 22, characterized in that the concentration of ammonium sulfate in the complex buffered solution is about 0.6 M and more preferred 0.6 M.

24. The method according to any of the items 1 to 23, characterized in that the stationary phase of step (f) is a solid phase matrix derivatized with hydrophobic organic residues.

25. The method according to item 24, characterized in that the stationary phase of step (f) is a solid phase matrix derivatized with an organic residue selected from the group consisting of hexyl, butyl, octyl and phenyl.

26. The method according to any of the items 24 and 25, characterized in that the solid phase matrix is selected from the group consisting of agarose, a methacrylate derivative, a polymerizate of acrylamide, a copolymerizate comprising acrylamide, a polymer derived from vinyl monomers (vinyl polymer) and a copolymerisate comprising styrene and divinylbenzene.

27. The method according to any of the items 24 to 26, characterized in that the stationary phase of step (f) is selected from the group consisting of TOYOPEARL Phenyl-650, Phenyl SEPHAROSE CL-4B, Phenyl SEPHAROSE 6 Fast Flow (High Sub) and Phenyl SEPHAROSE 6 Fast Flow (Low Sub).

28. The method according to item 27, characterized in that the stationary phase of step (1) is Phenyl SEPHAROSE 6 Fast Flow (Low Sub).

29. The method according to any of the items 1 to 28, characterized in that step (f) is followed by a further step (f') comprising washing the stationary phase of step (f) with an aqueous washing buffer comprising $Ca^{2+}$ ions and with a neutral pH and a conductivity of between 50 mS/cm and 300 mS/cm, whereby collagenase type I and type II proteins remain adsorbed to the stationary phase.

30. The method according to item 29, characterized in that the conductivity of the washing buffer is the same as the conductivity of the complex buffered solution of step (d).

31. The method according to any of the items 29 and 30, characterized in that the concentration of $Ca^{2+}$ ions and/or the concentration of ammonium sulfate and/or the pH of the washing buffer are the same as in the complex buffered solution of step (d).

32. The method according to any of the items 29 to 31, characterized in that step-(g) is performed by eluting the collagenase type I and type II proteins from the stationary phase of step (f').

33. The method according to any of the items 1 to 32, characterized in that step (g) is performed with an elution buffer, whereby the elution buffer contains salt in a lower concentration and a lower conductivity than in the complex buffered solution.

34. The method according to item 33, characterized in that step (g) is performed by applying a salt concentration gradient to the stationary phase.

35. The method according to item 33, characterized in that step (g) is performed by applying one or more elution buffers and performing isocratic elution.

36. The method according to item 33, characterized in that step (g) the collagenase type I and type II proteins are eluted by applying an elution buffer to the stationary phase, whereby the conductivity of the elution buffer is about 20% below the conductivity of the complex buffered solution.

37. The method, according to item 36, characterized in that the conductivity of the elution buffer is about 76 mS/cm.

38. The method according to any of the items 1 to 37, characterized in that the complex mixture comprises further enzymes with proteolytic activity.

39. The method according to item 38, characterized in that the complex mixture comprises an enzyme with proteolytic activity selected from the group consisting of clostripain (Endoproteinase Arg-C, EC 3.4.22.8), a neutral protease, and an enzyme with tryptic activity.

40. The method according to any of the items 38 and 39, characterized in that the complex mixture is the supernatant or the filtrate of a liquid *Clostridium histolyticum* culture.

41. The method according to any of the items 1 to 40, characterized in that the collagenase type I and type II proteins obtainable in step (g) and optionally a subsequent step removal of ammonium sulfate are enzymatically active.

42. The method according to any of the items 1 to 41, characterized in that step (g) is followed by a subsequent step, whereby in the subsequent step ammonium sulfate is separated from the collagenase type I and type II proteins.

43. The method according to any of the items 1 to 42, characterized in that the collagenase type I and type II proteins after the elution of step (g) are further purified by cation exchange chromatography, whereby further residual proteolytic activity is further separated from the collagenase type I and type II proteins.

44. The method according to item 43, characterized in that the cation exchange chromatography is performed in the presence of $Ca^{2+}$ ions at a concentration of about 5 mM, a buffer compound, and at a neutral pH.

45. The method according to any of the items 43 and 44, characterized in that the concentration of the buffer compound is 20 mM.

46. The method according to item 45, characterized in that the buffer compound is selected from the group consisting of BES, Tris, BisTris, BisTris propane, HEPES, MES, MOPS, MOPSO, PIPES, TAPS, TES, TEA, and Tricine.

47. The method according to item 46, characterized in that the buffer compound is TES or HEPES.

48. The method according to item 44, characterized in that the cation exchange chromatography is performed in the presence of $CaCl_2$ at a concentration of about 5 mM.

49. The method according to any of the items 43 to 48, characterized in that the cation exchanging stationary phase is SP SEPHAROSE.

50. The method according to any of the items 43 to 49, characterized in that the collagenase type I and type II proteins are separated by performing the steps
    (a) contacting the further purified collagenase type I and type II proteins with an anion exchanging stationary phase, and adsorbing the collagenase type I and type II proteins to the stationary phase; and
    (b) eluting, in separate fractions, collagenase type I and collagenase type II proteins from the stationary phase of step (a);
    whereby collagenase type I and collagenase type II proteins are purified separately.

51. The method according to item 50; characterized in that step (a) is performed in the presence of $Ca^{2+}$ ions at a concentration of about 5 mM, a buffer compound, and at a neutral or weakly alkaline pH.

52. The method according to any of the items 50 and 51, characterized in that step (b) is performed using gradient elution applying a 1×-25× concentration gradient of an elution buffer comprising, at the 1× concentration, $Ca^{2+}$ ions at a concentration of about 35 mM, a buffer compound, and a neutral or weakly alkaline pH, whereby 1× is the starting concentration and 25× is the end concentration of the gradient.

53. The method according to any of the items 51 and 52, characterized in that the weakly alkaline pH is 7.5.

54. Method according to any of the items 51 and 52, characterized in that the concentration of the buffer compound is 5 mM.

55. Method according to item 54, characterized in that the buffer compound is selected from the group consisting of BES, Tris, BisTris, BisTris propane, HEPES, MES, MOPS, MOPSO, PIPES, TAPS, TES, TEA, and Tricine.

56. The method according to item 55, characterized in that the buffer compound is TES or HEPES.

57. The method according to item 51, characterized in that step (A) is performed in the presence of $CaCl_2$ at a concentration of about 5 mM.

58. The method according to item 52, characterized in that in step (B) the elution buffer, at the 1× concentration, comprises $CaCl_2$ at a concentration of about 35 mM.
59. The method to any of the items 50 to 58, characterized in that the anion exchanging stationary phase is Q-SEPHAROSE.
60. The method according to any of the items 43 to 59, characterized in that the collagenase type I and type II proteins obtainable in step (b) are enzymatically active.
61. The method according to any of the items 50 to 60, characterized in that the collagenase type I and type II proteins are obtained in separate fractions.
62. Preparation comprising enzymatically active *Clostridium histolyticum* collagenase type I and type II proteins, obtainable by the method according to any of the items 1 to 42.
63. The preparation according to item 62, characterized in that in said preparation the tryptic proteolytic activity is reduced by a factor of between about 100 and about 400, compared to the complex mixture of the supernatant or filtrate of the liquid *Clostridium histolyticum* culture.
64. Purified preparation of enzymatically active *Clostridium histolyticum* collagenase type I, obtainable by the method according to item 61.
65. Purified preparation of enzymatically active *Clostridium histolyticum* collagenase type I according to item 64, characterized in that about 82% of the collagenase type I protein in the preparation has a molecular weight of 113,920 Da, determined by LC ESI-MS.
66. Purified preparation of enzymatically active *Clostridium histolyticum* collagenase type I according to item 65, characterized in that about 82% of the collagenase type I protein is N-terminally intact.
67. Purified preparation of enzymatically active *Clostridium histolyticum* collagenase type I according to item 66, characterized in that the N-terminus of the collagenase type I protein has the amino acid sequence IANTNS (SEQ ID NO: 1).
68. Purified preparation of enzymatically active *Clostridium histolyticum* collagenase type II, obtainable by the method according to item 61.
69. Purified preparation of enzymatically active *Clostridium histolyticum* collagenase type II according to item 68, characterized in that about 93% of the collagenase type II protein in the preparation has a molecular weight of 112,000 Da, determined by LC ESI-MS.
70. Purified preparation of enzymatically active *Clostridium histolyticum* collagenase type II according to item 69, characterized in that about 93% of the collagenase type II protein is N-terminally intact.
71. Purified preparation of enzymatically active *Clostridium histolyticum* collagenase type II according to item 70, characterized in that the N-terminus of the collagenase type II protein has the amino acid sequence VQNESK (SEQ ID NO: 2).
72. Purified preparation of enzymatically active *Clostridium histolyticum* collagenase type I according to any of the items 64 to 67, characterized in that the activity of clostripain in the preparation is less than about 0.04 U/mg of protein and more preferred between about 0.01 U/mg of protein and about 0.03 U/mg of protein.
73. Purified preparation of enzymatically active *Clostridium histolyticum* collagenase type II according to any of the items 68 to 71, characterized in that the activity of clostripain in the preparation is less than about 0.07 U/mg of protein and more preferred between about 0.04 U/mg of protein and about 0.06 U/mg of protein.
74. Purified preparation of enzymatically active *Clostridium histolyticum* collagenase type I according to any of the items 64 to 67, characterized in that the activity of trypsin in the preparation is less than about 0.0003 U/mg of protein and more preferred between about 0.0001 U/mg of protein and about 0.0003 U/mg of protein.
75. Purified preparation of enzymatically active *Clostridium histolyticum* collagenase type II according to any of the items 68 to 71, characterized in that the activity of trypsin in the preparation is less than about 0.001 U/mg of protein and more preferred between about 0.0003 U/mg of protein and about 0.001 U/mg of protein.
76. Blend comprising *Clostridium histolyticum* collagenase type I and *Clostridium histolyticum* collagenase type II, characterized in that a first measured amount of a purified preparation according to any of the items 64 to 67 is mixed with a second measured amount of a purified preparation according to any of the items 68 to 71.
77. The blend according to item 76, characterized in that the blend additionally comprises a third measured amount of a preparation of a further proteolytic enzyme.
78. Use of a purified preparation of enzymatically active *Clostridium histolyticum* collagenase type according to any of the items 64 to 67 and any of the items 72 and 74 for processing a tissue sample, whereby collagen present in the sample is digested.
79. Use of a purified preparation of enzymatically active *Clostridium histolyticum* collagenase type II according to any of the items 68 to 71 and any of the items 73 and 75 for processing a tissue sample, whereby collagen present in the sample is digested.
80. Use of a blend according to any of the items 76 and 77 for processing a tissue sample, whereby collagen present in the sample is digested.

The following examples and figures are provided to aid the understanding of the present invention, the true scope of which is set forth in the appended claims. It is understood that modifications can be made in the procedures set forth without departing from the spirit of the invention.

EXAMPLE 1

Raw Materials Containing *C. histolyticum* Collagenase Type I and Type II Proteins The preferred raw material was a cleared supernatant of a *C. histolyticum* liquid culture. Liquid media supporting growth of *C. histolyticum* in culture are well known to the art. Recent literature on such media includes WO 2007/089851. With regards to removal of unwanted proteolytic activities and the purity of the final preparations of the collagenase proteins, no significant differences were observed for different growth media when using the purification scheme of the invention as described below.

In a stepwise upscaling process, *C. histolyticum* was grown anaerobically in liquid culture under a nitrogen atmosphere. A first seed culture typically started with a volume of about 100 ml. Subsequent pre-cultures were made stepwise with increased volumes, e.g., 1 l, 10 l, 50 l. Large scale fermentation was carried out with culture volumes ranging from about 100 l to about 2,500 l. The growth temperature was 30° C. and pH of the fermentation medium was kept at a value of about 7.3. At regular intervals samples of the culture were drawn and the supernatant was tested for collagenase proteolytic activity as described in Example 2. Typically, a large-scale fermenter was harvested between about 15 h and about 18 h after addition of the pre-culture.

Upon termination of fermentation the culture was cooled to a temperature between about 2° C. and 8° C. Cellular material, debris particles and other particulate matter was separated from the liquid medium by either centrifugation or filtration, both resulting in a cleared culture supernatant. In the case of filtration, the filtrate was passed through filter material with a pore size of between about 0.3 µm to about 1 µm. Good results were obtained with ACROPAK 500 material (pore size 0.45-0.8 µm). (Acropak is a registered trademark of Atek Manufacturing, LLC.)

Prior to subsequent purification steps, several proteolytic activities were assayed in the cleared culture supernatant. These included the proteolytic activities of collagenases (see Example 2), clostripain (see Example 3), and trypsin (see Example 4). Protein content was determined by conventional means, typically using UV spectroscopy, the Bradford-Lowry- or biuret protein assays, or the bicinchoninic acid assay. A typical cleared culture supernatant had a protein content of about 1.5 g/l and a collagenase activity of about 4 kU/l.

Alternatively, raw preparations such as lyophilisates of culture supernatants (Bond, M., D., van Ward, H., E., Biochemistry 23 (1984) 3077-3085) can serve as starting material. In this case, an aqueous solution of a lyophilisate is processed according to the invention as described further below.

EXAMPLE 2

Assay to Determine Collagenase I and II Proteolytic Activity

Collagenase proteolytic activity was measured by a standard method in Wünsch units (Wuensch, E., Heidrich, H., Z., Physiol. Chem. 333 (1963) 149-159) using a synthetic peptide substrate. Collagenase proteolytic activity catalyses the hydrolysis of the modified substrate ("Wuensch") peptide 4-phenylazo-benzyloxycarbonyl-Pro-Leu-Gly-Pro-Arg (SEQ ID NO: 3) (Bachem M1715) between the Leu and the Gly residue. One unit (U) of activity is defined by the hydrolysis of 1 µM peptide per minute at 25° C., pH 7.1.

The substrate peptide (also referred to as "substrate") was provided in a solution and at a concentration of 1 mg/ml. 10 mg substrate peptide were first dissolved in 0.2 ml methanol. The volume of the solution was increased to 10 ml by adding 0.1 M TrisHCl, pH 7.1. Further reagents were a 0.1 M $CaCl_2$ solution in water and an extraction mixture consisting of 5 volume parts ethyl acetate and 1 volume part 0.025 M citric acid in water. Drying tubes were provided as test tubes containing 0.35-0.4 g $Na_2SO_4$. Before use each drying tube was sealed with parafilm.

Control and sample reactions were set up in test tubes according to the following pipetting scheme and workflow:

| Step | Solution | Control test tube | Sample test tube |
|------|----------|-------------------|------------------|
| 1 | Substrate peptide | 1 ml | 1 ml |
|   | $CaCl_2$ | 0.2 ml | 0.2 ml |
|   | Mix, warm to 25° C. | | |
| 2 | Sample material[§] | — | 0.05 ml |
|   | 0.1M TrisHCl, pH 7.1 | 0.05 ml | — |
|   | Mix, incubate for 15 min at 25° C.; after incubation an aliquot of the incubated solution is transferred to a volume of the extraction mixture | | |
| 3 | Incubated solution of step 2 | 0.5 ml | 0.5 ml |
|   | Extraction mixture | 6 ml | 6 ml |
|   | Mix immediately by vortexing for 20 s, transfer about 3 ml of ethyl acetate phase into a drying tube, mix by vortexing and transfer supernatant into cuvette; measure extinction (A) at 320 nm, cuvette light path = 1 cm. | | |

-continued

| Step | Solution | Control test tube | Sample test tube |
|------|----------|-------------------|------------------|
| 4 | Calculate volume activity [U/ml] = ΔA * d * 0.794 | | |
|   | A: measured extinction value | | |
|   | d: dilution factor | | |
|   | $\Delta A = A_{sample} - A_{control}$ | | |

[§]a solution comprising either both, collagenase type I and type II enzymes altogether or a solution comprising either of the enzymes separately. Sample material used in the assay was usually prepared by diluting a solution comprising collagenase type I and/or type II. Dilutions were made with with 0.1M TrisHCl, pH 7.1; for each measurement the respective dilution factor (d) was adjusted and chosen in order to finally result in an extinction value between 0.3 and 1.0. Solutions with collagenase type I but not type II were diluted 1:100; solutions comprising collagenase type II were diluted 1:1,000. Additionally, standards with known amounts of collagenase type I and/or type II were tested as references.

In mixtures containing both collagenase type I and type II enzymes the measured activity of collagenase II was always greater than the activity of collagenase I, when performing activity assays using the Wuensch peptide as a substrate. Collagenase type II purified following the complete purification scheme according to the invention and obtained as a final product as described in Example 14 had a specific activity of between about 10 and about 14 U per mg of protein; the specific activity of the likewise purified collagenase type I was between about 0.1 and about 0.3 U per mg of protein.

EXAMPLE 3

Assay to Determine Clostripain Proteolytic Activity

Clostripain proteolytic activity was measured by a method using a synthetic substrate. Clostripain proteolytic activity catalyses the hydrolysis of Benzoyl-L-arginine ethyl ester (also referred to as "BAEE"), thereby forming Benzoyl-L-arginine and ethanol. The reaction is specific for clostripain and the substrate is converted only to a very limited extent by collagenase proteolytic activity.

The synthetic substrate (also referred to as "substrate") was provided in a solution and at a concentration of 38 mM dissolved in 0.1 M potassium phosphate buffer pH 7.6 ("PPB"). Further reagents were PPB, 194 mM dithiothreitol ("DTT") dissolved in PPB, and 0.01 M $CaCl_2$ solution.

Control and sample reactions were set up in test tubes according to the following pipetting scheme and workflow:

| Step | | | |
|------|--|--|--|
| 1 | Buffer/substrate solution: 0.73 mM BAEE, 7.8 mM DTT, 0.4 mM $CaCl_2$ 0.5 ml BAEE solution, 1 ml DTT solution, 1 ml $CaCl_2$ solution are pipetted into a 25 ml flask; PPB is added to the 25 ml mark; the solution is mixed. | | |
| 2 | Sample material and standards are provided as lyophilized solid dry matter ("sample"). Immediately before measurement 1 mg of each sample is dissolved in 1 ml repurified (HPLC grade) water and diluted by adding 49 volume parts of PPB to 1 volume part of dissolved sample. | | |
|   | Solution | Control test tube | Sample test tube |
| 3 | PPB | 0.05 ml | — |
|   | Buffer/substrate solution | 3 ml | 3 ml |
|   | Mix, incubate and warm to 25° C. | | |
| 4 | Start enzymatic reaction by adding Sample | — | 0.05 ml |
|   | Mix, determine extinction (A) at 255 nm, cuvette light path = 1 cm; monitor the change of extinction and determine ΔA/min based on the linear range of the curve | | |

-continued

| Step | |
|---|---|
| 5 | Calculate volume activity [U/ml] = 3.05/($\epsilon_{255}$ * 0.05 * 1) * ΔA/min<br>Volume activity in sample solution<br>Any dilution factor is to be taken into account when calculating volume activity<br>A: measured extinction value<br>ΔA = $A_{sample} - A_{control}$<br>$\epsilon_{255} = 0.81 [1 * mM^{-1} * cm^{-1}]$ |

The reaction velocity is measured as an increase in absorbance at 255 nm resulting from the hydrolysis of the substrate BAEE. 1 U of clostripain proteolytic activity hydrolyzes 1 μM of BAEE per minute at 25° C. and pH 7.6 under the conditions as specified above.

EXAMPLE 4

Assay to Determine Tryptic Proteolytic Activity

Trypsin preferentially hydrolyzes bonds whose carboxyl groups are contributed by Lys or Arg. Trypsin proteolytic activity was measured by a method using a synthetic substrate. Trypsin proteolytic activity catalyses the hydrolysis of Cromozym TRY, also referred to as Z-Val-Gly-Arg-4-nitroanilin, thereby forming Z-Val-Gly-Arg and 4-nitroanilin ("4-NA").

The synthetic substrate (also referred to as "substrate") was provided in a solution and at a concentration of 10 mM dissolved in ultrapure water. A further reagent was 0.02 M $CaCl_2$, 0.1 M TrisHCl, pH 8.

Control and sample reactions were set up in test tubes according to the following pipetting scheme and workflow:

| Step | | | |
|---|---|---|---|
| 1 | Working solution: Mix 12.88 volume parts 0.02M $CaCl_2$, 0.1M TrisHCl, pH 8 and 1.4 volume parts 10 mM substrate solution; dispense 1.02 ml aliquots into cuvettes; warm to 25° C. | | |
| 2 | Start enzymatic reaction by adding | | |
| | Solution | Control test tube | Sample test tube |
| | Sample§ or control | 0.1°ml<br>(working solution) | 0.1 ml<br>(sample liquid) |
| 3 | Mix, determine extinction (A) at 405 nm, cuvette light path = 1 cm; monitor the change of extinction for at least 5 min and determine ΔA/min based on the linear range of the curve | | |
| 4 | Calculate volume activity [U/ml] = 1.12/($\epsilon_{405}$ * 0.1 * 1) * ΔA/min<br>ΔA = $A_{sample} - A_{control}$<br>Total enzyme activity in enzyme solution: multiply ΔA/min with the dilution factor<br>$\epsilon_{405} = 10.4 [1 * mM^{-1} * cm^{-1}]$ | | |

§the sample usually consists of an undiluted sample liquid, such as culture supernatant and an aliquot of a fraction of a flow-through of a chromatographic column.

The reaction velocity is measured as an increase in absorbance at 405 nm resulting from the hydrolysis of the substrate. 1 U of Trypsin proteolytic activity hydrolyzes 1 μM of Cromozym TRY per minute at 25° C. and pH 8 under the conditions as specified above.

EXAMPLE 5

Analytical Mono Q HPLC Assay

Sampled aliquots of preparative chromatographic fractions were analyzed by way of HPLC using a Mono Q column. In case both, collagenase type I and type II proteins are present, Mono Q chromatography allows to separate the proteins. Protein quantities and integrity can be assessed on the basis of Mono Q chromatograms recorded, e.g., with a UV spectrometer.

HPLC analysis was performed using a Mono Q 5/50 column (GE, code no. 17-5166-01). Prior to applying a sample the column was equilibrated with 1 mM $CaCl_2$, 20 mM TrisHCl, pH 7.5 ("Buffer A", 10 column volumes). A sample which usually included collagenase type I and II proteins was applied and bound to the ion exchanger material, followed by washing with 3 column volumes of Buffer A. Elution was performed using 30 column volumes of elution buffer comprising a linear concentration gradient starting with Buffer A, and ending with 1 M NaCl, 1 mM $CaCl_2$, 20 mM TrisHCl, pH 7.5 ("Buffer B") at a 15% concentration. Further undesired (foreign) proteins eluted in the concentration interval above 15% and until 100% of Buffer B. Afterwards, the column was re-conditioned by passing 8 column volumes of Buffer A through the column.

For detection a UV-Spectrometer was used. Absorption was monitored at a wavelength of 280 nm.

EXAMPLE 6

Mass Spectrometric Analysis of Collagenase Proteins

Analysis of purified proteins was performed by HPLC/ESI-MS: Proteins were separated by way of reversed phase HPLC using an Alliance HT (Waters) instrument or a comparable unit. The preferred column was a Vydac C18, Protein & Peptide, 250*2.1 mm 218 TP 52 (Macherey & Nagel, Germany). Proteins were detected online with a UV detector at 226 nm. In scan mode proteins were detected by way of electrospray mass spectrometry (ESI-MS) using a QTOF II (Waters) instrument.

Samples were adjusted to a protein concentration of 1 mg/ml in water. For each run, 10 μl of protein solution were injected and analyzed. Between two analytical runs two mock samples (10 μl) consisting just of water were injected, in order to avoid cross-contamination.

Figure 4:
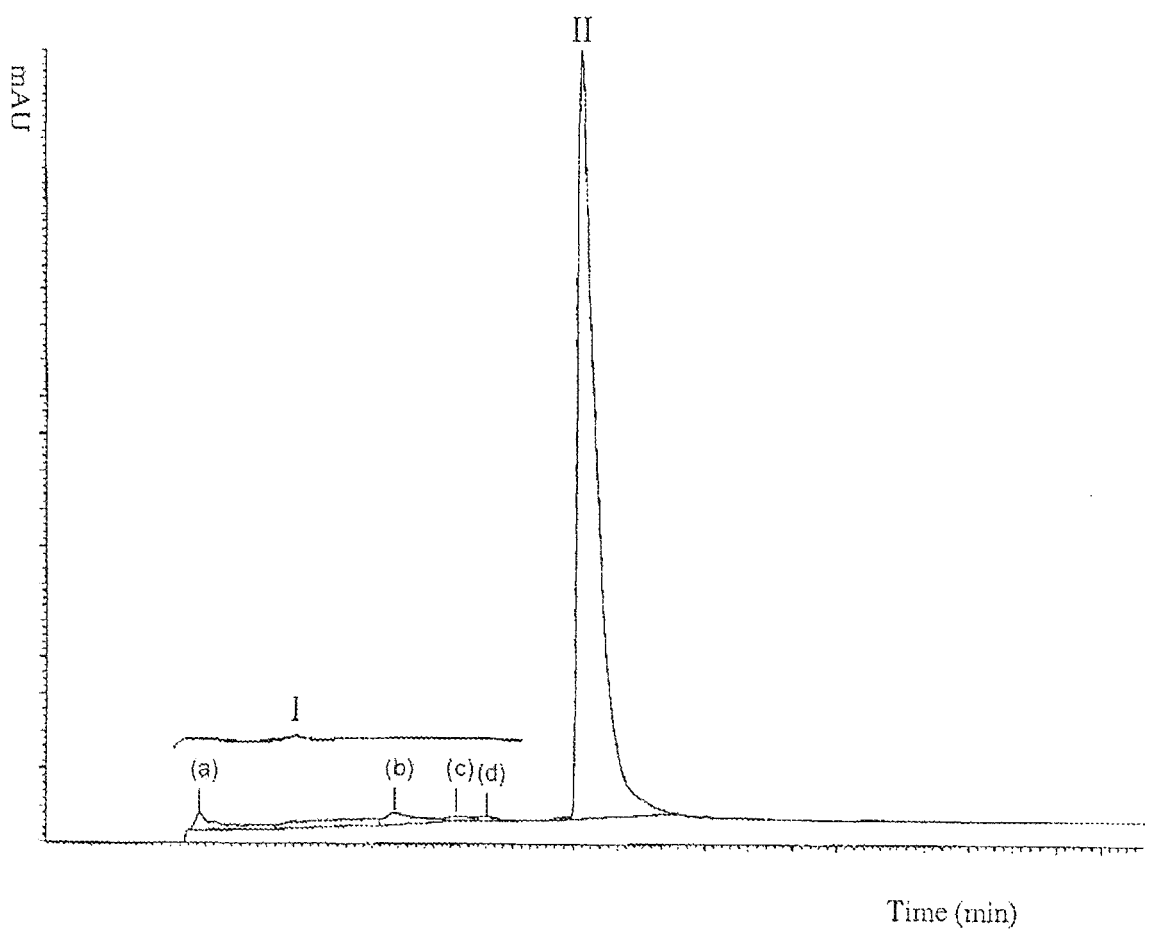
FIG. 4 Exemplary HPLC/ESI-MS results for purified collagenase type I. Ordinate: mAU, abscissa: time. Peak heights of group I peaks (indicated as "I") were between about 1180 units and about 4720 units. In comparison, the height of the main peak of group II (indicated as "II") was about 207527 units. Marked peaks with peak heights above baseline: (a) 3.47 min, 4718 mAU; (b) 7.94 min, 3342 mAU; (c) 9.32 min, 1425 mAU; (d) 10.00 min, 1184 mAU.

FIG. 4 shows the results for a collagenase type I preparation. Two groups of peaks were obtained as indicated in FIG. 4. Group II represented about 90% of the total peak area. The main peak within group II corresponded to a molecular weight of 113,930 Da accounting for 82% of the total peak area. A minor peak within group II corresponded to a molecular weight of 113,410 Da accounting for 8% of the total peak area.

Figure 5:
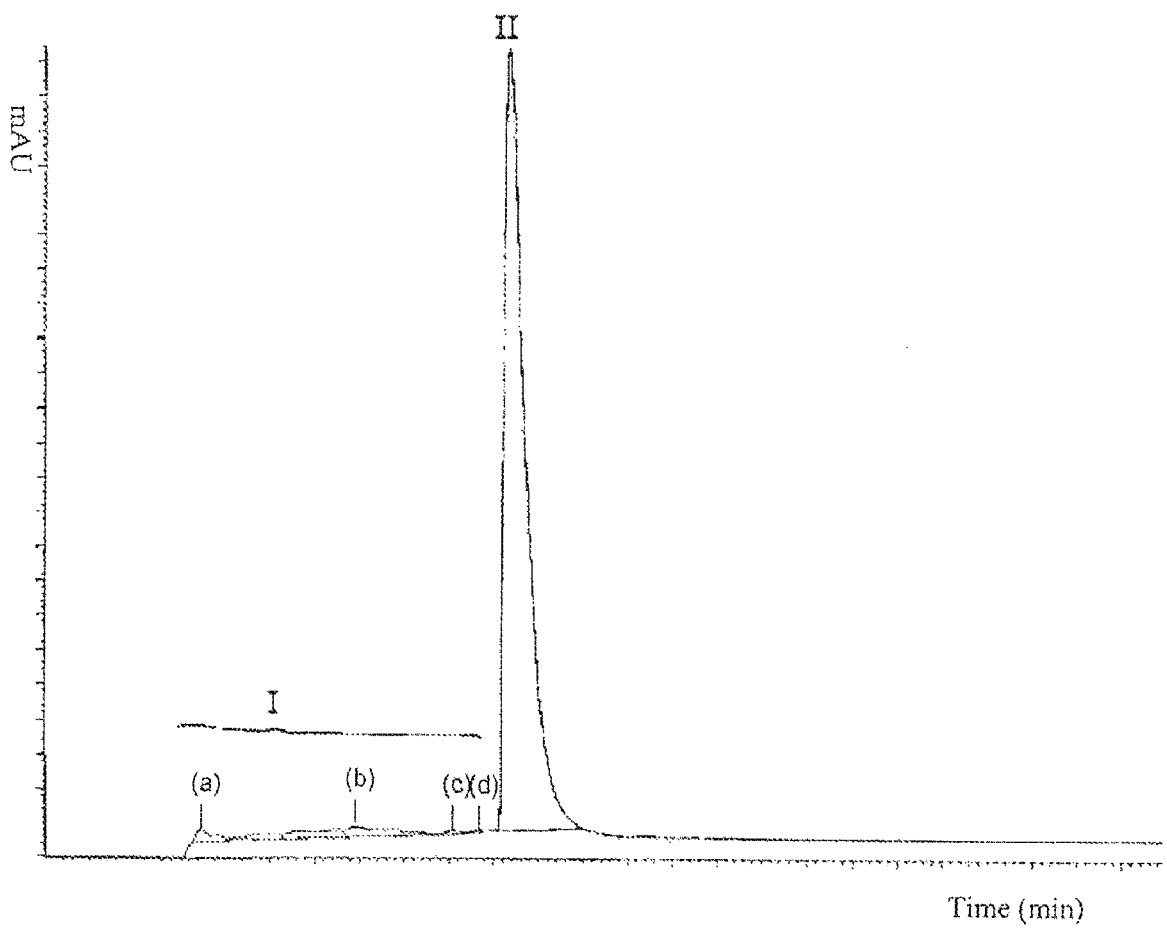
FIG. 5 Exemplary HPLC/ESI-MS results for purified collagenase type II. Ordinate: mAU, abscissa: time. Peak heights of group I peaks (indicated as "I") were between about 840 units and about 3840 units. In comparison, the height of the main peak of group II (indicated as "II") was about 226388 units. Marked peaks with peak heights above baseline: (a) 3.47 min, 3835 mAU; (b) 6.87 min, 3084 mAU; (c) 9.12 min, 1134 mAU; (d) 9.64 min, 848 mAU.

FIG. 5 shows the results for a collagenase type II preparation. Two groups of peaks were obtained as indicated in FIG. 5. Group II represented about 93% of the total peak area consisting of a single main peak. The peak corresponded to a molecular weight of 112,000 Da.

EXAMPLE 7

Preparation of *C. histolyticum* Collagenase Type I and Type II Proteins Using Red SEPHAROSE, SP SEPHAROSE Chromatography and Q SEPHAROSE Chromatography All steps described in the following were performed at a temperature of between about 2° C. and about 8° C., if not indicated otherwise. A cleared culture supernatant was obtained as described in Example 1. In a first step, ammonium sulfate was dissolved in the supernatant at a concentration of about 1.65 M. In an exemplary case, 245.65 g of ammonium sulfate were dissolved per 1 of supernatant and incubated for between about 8 h and about 24 h. The precipitate was separated from the liquid phase by centrifugation or by filtration. The cleared liquid phase was subsequently diafiltrated against 0.02 M HEPES, 1 mM $CaCl_2$, pH 7 (in the following also referred to as "Buffer R1"); following diafiltration the conductivity of the liquid phase was adjusted to a value of below 2 mS/cm, whereby the liquid phase was diluted with additional Buffer R1 if necessary. The pH of the liquid phase was adjusted to a value of between 6.8 and 7.0 with Tris/HEPES buffer.

Protein content was determined by measuring the extinction of a 1:20 dilution of the liquid phase at 280 nm. Additionally the liquid phase was analyzed using Mono Q HPLC as described in Example 5.

During the following chromatography steps the pH of any mobile phase was kept at pH 7±0.2, if not indicated otherwise. A preparative Red SEPHAROSE Fast Flow column equilibrated with Buffer R1 was loaded with the liquid phase and subsequently washed with 2 or more column volumes of Buffer R1, until the optical density at 280 nm of the effluent from the column reached a base line which did not change significantly anymore. The base line thus finally reflected only small quantities of protein in the washing buffer. Subsequently, the column was eluted with an elution buffer containing 0.02 M TrisHCl, 1 mM $CaCl_2$, 1 M NaCl, pH 9 (in the following also referred to as "Buffer R2"). The eluate was collected and diafiltrated against 20 mM HEPES, 5 mM $CaCl_2$, pH 7 (in the following also referred to as "Buffer S1"); the protein content of the liquid, phase was adjusted to 5 mg/ml and the conductivity was adjusted to a value of below 2 mS/cm, whereby the liquid phase was diluted with additional Buffer S1 if necessary.

In a following step, a preparative SP SEPHAROSE chromatography was performed. In order to condition the column material, the SP SEPHAROSE column was firstly washed with water; afterwards, half a column volume of 0.5 M $CaCl_2$ and 2.5 column volumes of 100 mM HEPES, 5 mM $CaCl_2$, pH 7 were passed through the column. Subsequently, the column was washed with Buffer S1; the column was equilibrated with Buffer S1 until the effluent had the pH (±0.2) of the diafiltrated and adjusted liquid phase obtained after Red SEPHAROSE chromatography. The SP SEPHAROSE column was subsequently loaded with said liquid phase comprising the collagenase proteins and further impurities. Following the loading step the column was washed with Buffer S1 and elution of proteins was monitored. Clostripain and the collagenase proteins were collected in separate fractions. The collagenase protein fraction was concentrated by diafiltration against 5 mM HEPES, 1 mM $CaCl_2$, pH 7.5 (in the following also referred to as "Buffer Q1").

Collagenase type I and type II proteins were separated in a subsequent preparative Q SEPHAROSE chromatography step. A Q SEPHAROSE ff column was firstly washed with water; afterwards, half a column volume of 4 M guanidinium HCl was passed through the column, followed by a further wash with water, one pass each with 0.5 M NaOH and 0.5 M HCl, a further wash with water and finally an equilibration of the column with Buffer Q1. The liquid phase containing the collagenase proteins obtained after SP SEPHAROSE chromatography was applied to the column. About 1-2 column volumes of Buffer Q1 were applied to the column and the flow-through was discarded. Collagenase type I and type II proteins were eluted separately by applying a concentration gradient comprising 25 column volumes, starting with a ratio of 95% Buffer Q1, 5% Buffer Q2 (5 mM HEPES, 35 mM $CaCl_2$, pH 7.5) and ending with a ratio of 5% Buffer Q1 and 95% Buffer Q2. Elution of proteins was monitored. Collagenase type I and II proteins were collected in separate fractions and verified using HPLC analytics (see Example 5).

EXAMPLE 8

Figure 3:
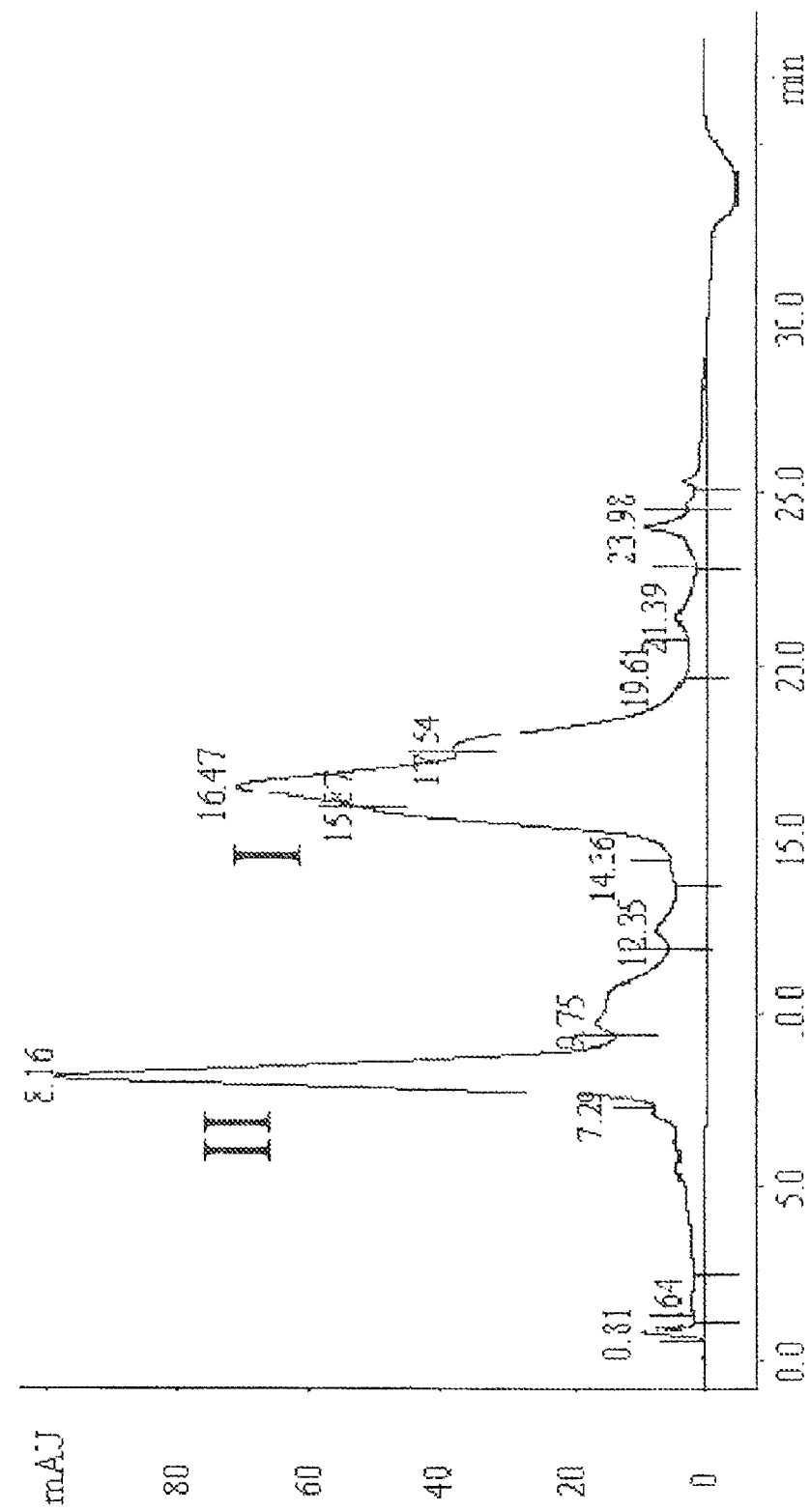
FIG. 3 Mono Q chromatogram (method see Example 5) of collagenase type II and type I proteins after Red SEPHAROSE Fast Flow chromatography (GE Healthcare Bio-Sciences AB). Peak designations as in FIG. 1.

Quantitative Determination of the Ratio of Collagenase Type II and I Proteins after Purification with Red SEPHAROSE Fast Flow Collagenase type I and II proteins were purified according to the method of Example 7. Mono Q analytics were performed as explained in Example 5. The integrals under the peaks corresponding to the collagenase type I and II proteins were quantified. To this end, FIG. 3 depicts an exemplary chromatogram. The quantification of the area under the peaks as shown is given in Table 1.

TABLE 1

Quantification of collagenase type I and II peak areas

| No | Retention time, min | Area mAU * min | Area/Peak area (time) % |
|---|---|---|---|
| 1 | 0.81 | 2.6433 | 0.87 |
| 2 | 1.64 | 2.0993 | 0.69 |
| 3 | 8.16 | 85.4644 | 28.13 |
| 4 | 9.75 | 31.2364 | 10.28 |
| 5 | 12.35 | 10.0797 | 3.32 |
| 6 | 15.87 | 30.8374 | 10.15 |
| 7 | 16.47 | 90.2817 | 29.71 |
| 8 | 17.54 | 36.8901 | 12.14 |
| 9 | 21.39 | 6.4197 | 2.11 |
| 10 | 23.98 | 6.3435 | 2.09 |
| 11 | 24.63 | 1.5335 | 0.50 |
| | | | Σ 99.99 |

The total peak area for collagenase type II protein is obtained from the interval between 7.29 min and 9.75 mm and accounts for 28.1% of the total peak area.

The peak in the interval between 9.75 min and 12.35 min accounting for 10.3% of the total peak area was disregarded. Mass spectrometric analysis showed that this peak area reflects a mixture of different collagenase type I degradation products and several non-collagenase proteins.

The total peak area for intact collagenase type I protein is obtained from the intervals between 14.36 min and 15.87 min, and accounts for 10.2% of the total peak area. Degradation products are detected in the intervals of 15.87 min and 17.54 min (29.7%), and 17.54 min and 19.61 min (12.1%). Taken together, the peak area related to collagenase type I accounts for 52% of the total peak area.

The ratio of type I/type II collagenase protein therefore corresponds to 52/28.1 which approximates the value of 1.85.

In the following, a novel method and workflow for the purification of collagenase type I and type II proteins are presented which particularly overcome the effects of degradation of the target proteins by other proteolytic activities.

EXAMPLE 9

Precipitation of Collagenase Type I and Type II Proteins from Cleared Culture Supernatant All steps described in the following were performed at a temperature in the range of between about 2° C. and about 8°

C., if not indicated otherwise. A measured amount of solid ammonium sulfate was added to a cleared culture supernatant which was obtained by ultrafiltration of a C. histolyticum liquid culture with ACROPAK 500 filter material (see Example 1). Ammonium sulfate was added to the supernatant stepwise over a period of between about 20 min and about 30 min, and dissolved by stirring until a final concentration of 3.2 M was reached. After the ammonium sulfate had dissolved completely, the precipitate was allowed to form for between about 10 min and about 20 min. Subsequently, the precipitated matter was isolated from the remaining liquid phase by centrifugation. The isolated precipitate was either directly redissolved for further purification steps (see the Example 10) or stored at between about 2 and about 8° C. for up to 2 weeks or at −20° C. for more than 2 weeks.

EXAMPLE 10

Hydrophobic Interaction Chromatography (HIC)

The isolated precipitate obtained by way of the procedure of Example 9 was dissolved in an aqueous buffer containing 5 mM $CaCl_2$, 20 mM HEPES, pH 7 and the conductivity of the solution was adjusted with ammonium sulfate to a value of about 95 mS/cm. The solution was applied to a chromatography column with Phenyl SEPHAROSE 6 Fast Flow (Low Sub) (General Electric, GE 17-0965-04) as the stationary phase. Before, the column was equilibrated with a buffer containing 0.6 M $(NH_4)_2SO_4$, 5 mM $CaCl_2$, 20 mM HEPES, pH 7.

While loading the mixture with the collagenase proteins on the column, the flow-through was discarded. Subsequently, the stationary phase with the bound collagenase proteins was washed using an aqueous washing buffer containing 0.6 M $(NH_4)_2SO_4$, 5 mM $CaCl_2$, 20 mM HEPES, pH 7, whereby the conductivity of the wash buffer was about 95 mS/cm. Typically, between 10 and 15 column volumes of washing buffer were passed through the column for the washing step. The washing buffer flow-through was discarded.

The collagenase proteins were removed from the stationary phase by performing isocratic elution with an elution buffer composed of 5 mM $CaCl_2$, 20 mM HEPES, pH 7, whereby the conductivity of the buffer was adjusted with ammonium sulfate to a value of 76 mS/cm. To this end, between 15 and 20 column volumes of elution buffer were passed through the column.

Alternatively, gradient elution was performed starting with 5 mM $CaCl_2$, 20 mM HEPES, pH 7, whereby the conductivity of the solution was adjusted with ammonium sulfate to a value of about 95 mS/cm ("Buffer 1"). The end concentration of the gradient was 5 mM $CaCl_2$, 20 mM HEPES, pH 7 ("Buffer 2") without ammonium sulfate. The total volume of the gradient typically was 10 column volumes. After gradient elution, the column was eluted with an additional 10 column volumes of Buffer 2.

The eluate or pooled fractions of the eluate comprising the collagenase proteins was/were subsequently subjected to concentration and diafiltration against 5 mM $CaCl_2$, 20 mM HEPES, pH 7.

EXAMPLE 11

Stability of Collagenase Proteins after Hydrophobic Interaction Chromatography

Aliquots of diafiltrated eluate obtained by the procedure of Example 10 were used for stability tests. Table 2 shows the effect of the reduction of clostripain and tryptic proteolytic activities. Comparable results were achieved in three independent preparation lots following hydrophobic interaction chromatography and using isocratic elution. Compared to the C. histolyticum culture supernatant, the tryptic ("tryp.") proteolytic activity was reduced by a factor of between about 100 and about 400, and the clostripain ("clos.") proteolytic activity was reduced by a factor of between about 100 and about 150.

TABLE 2

Reduction of unwanted proteolytic activities

| Preparation lot | 1 | | 2 | | 3 | |
|---|---|---|---|---|---|---|
| Proteolytic activities | clos. | tryp. | clos. | tryp. | clos. | tryp. |
| Reduction factor | 100 | 385 | 150 | 208 | 90 | 100 |

The stability of the collagenase type I and type II proteins in the preparation at this item was remarkably high, already. Mono Q analytics were performed as described in Example 5 to characterize the eluate(s). FIG. 1 shows an overlay of four chromatograms. Samples analyzed directly after hydrophobic interaction chromatography and following an incubation for 2 d, 3 d and 6 d at 4° C. were compared. As can be seen in FIG. 1, the main peak corresponding to collagenase type II protein did not markedly change in height and the integral under the peak did not change detectably. Taking the integral under the main peak corresponding to collagenase type I protein at 0 d as a reference (100%) there is only a slight gradual decrease after 2 d (about 99%), 3 d (about 98%) and 6 d (about 85%). Nevertheless, even after 6 days approximately the largest part of the total collagenase type I protein remained intact as evidenced by the integral under the peak.

This unexpected result shows that most of the unwanted proteolytic activities which lead to loss or shortening' of the desired proteins were already removed at this stage of the purification workflow. Early removal of the unwanted proteolytic activities was found to be crucial for further optimization of the recovery of collagenase type I protein.

EXAMPLE 12

Figure 2:
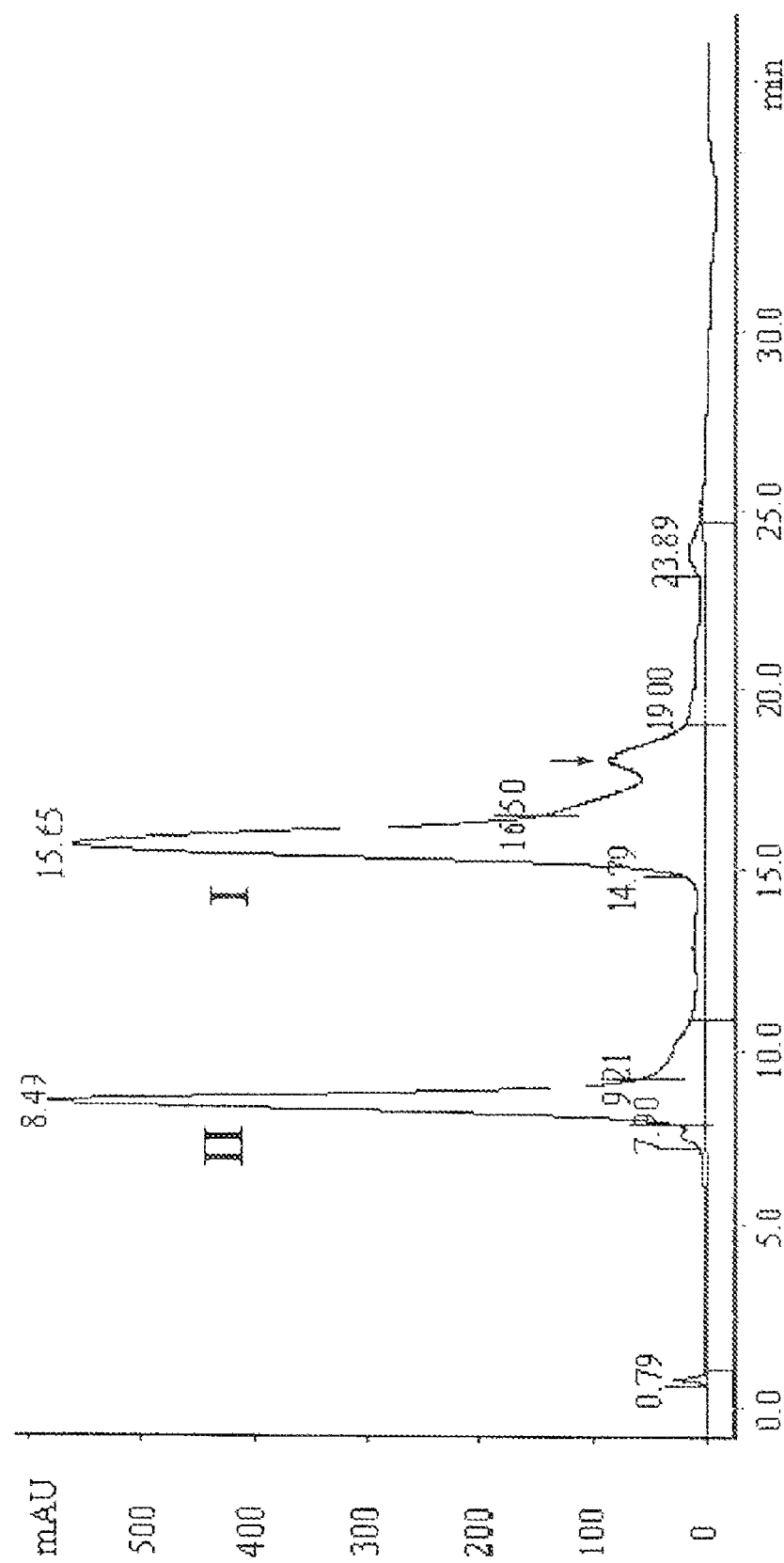
FIG. 2 Mono Q chromatogram (method see Example 5) of collagenase type II and type I proteins after hydrophobic interaction chromatography. Peak designations as in FIG. 1.

Quantitative Determination of the Ratio of Collagenase Type II and I Proteins after Hydrophobic Interaction Chromatography Following after hydrophobic interaction chromatography as described in Example 10, the ratio of collagenase type I and II proteins was determined. Mono Q analytics were performed as described in Example 5. The integrals under the peaks corresponding to the collagenase type I and II proteins were quantified. To this end, FIG. 2 depicts an exemplary chromatogram. The quantification of the area under the peaks as shown is given in Table 3.

TABLE 3

Quantification of collagenase type I and II peak areas

| No | Retention time, min | Area mAU * min | Area/Peak area (time) % |
|---|---|---|---|
| 1 | 0.79 | 4.1512 | 0.38 |
| 2 | 7.90 | 12.1344 | 1.10 |
| 3 | 8.49 | 336.0089 | 30.40 |
| 4 | 9.21 | 49.1216 | 4.44 |
| 5 | 15.65 | 509.8739 | 46.13 |

TABLE 3-continued

Quantification of collagenase type I and II peak areas

| No | Retention time, min | Area mAU * min | Area/Peak area (time) % |
|---|---|---|---|
| 6 | 16.50 | 179.8359 | 16.27 |
| 7 | 23.89 | 14.1003 | 1.28 |
| | | | Σ 100 |

The total peak area for collagenase type II protein is obtained from the interval between 7.90 min and 9.21 min and accounts for 30.4% of the total peak area.

The total peak area for intact collagenase type I protein is obtained from the interval between 14.79 min and 16.50 min and accounts for 46.1% of the total peak area. Due to proteolytic attack there are additional C-terminally shortened forms of collagenase type I protein in the interval between 16.50 min and 19.00 min which account for 16.3% of the total peak area. Thus, the aggregate peak area for collagenase type I protein is 62.4%.

The ratio of type I/type II collagenase protein therefore corresponds to 62.4/30.4 which approximates the value of 2.

EXAMPLE 13

Cation Exchange Chromatography

Residual clostripain and other unwanted proteolytic activities were removed from the mixture of collagenase type I and II proteins obtained by the procedure described in Example 10 by means of cation exchange chromatography. A cation exchange chromatography column (SP SEPHAROSE Fast Flow resin, Amersham Biosciences) was equilibrated with an aqueous buffer containing 5 mM $CaCl_2$, 20 mM HEPES, pH 7. The diafiltrated eluate obtained in Example 10 was applied to the chromatography column and the collagenase type I and II proteins were chromatographed through the stationary phase using the equilibration buffer as the mobile phase. The effluent from the column was collected in fractions. Fractions containing collagenase activity (assay see Example 2) were pooled.

EXAMPLE 14

Separation of Type I and Type II Collagenase Proteins Using Anion Exchange Chromatography Purified collagenase proteins obtained by the procedure of Example 13 were separated into type I and type II collagenase proteins. A Q SEPHAROSE Fast Flow anion exchange chromatography chromatography column was equilibrated with an aqueous buffer containing 5 mM $CaCl_2$, 5 mM. HEPES, pH 7.5. The mixture containing collagenase type I and II proteins obtained after the purification step of Example 13 was loaded on the column and adsorbed to the stationary phase. Subsequently, washing step was performed by passing 3 column volumes of the equilibration buffer through the column. Elution was performed by applying 25 column volumes of a linear $Ca^{2+}$ ion concentration gradient. Elution started with 5 mM $CaCl_2$, 5 mM HEPES, pH 7.5 ("Buffer I") and ended with 35 mM $CaCl_2$, 5 mM HEPES, pH 7.5 ("Buffer II"). Collagenase type I and type II proteins were obtained in separate fractions. Collagenase type I eluted at a Buffer I/Buffer II ratio of between about 44%/56% and about 6%/94%; collagenase type II eluted at a Buffer I/Buffer II ratio of between about 76%/24% and about 67%/33%.

EXAMPLE 15

Determination of N-terminal Amino Acids of Purified Type I and Type II Collagenase Proteins Separately obtained type I and type II collagenase proteins (see Example 14) were subjected to N-terminal sequencing of amino acids by way of Edman degradation and analysis using a PROCISE Sequencer (Applied Biosystems).

For the protein isoform corresponding to the most abundant Collagenase type I protein species in the preparation of Collagenase type I, the N-terminal sequence I-A-N-T-N-S (SEQ ID NO: 1) was detected.

For the protein isoform corresponding to the most abundant Collagenase type II protein species in the preparation of Collagenase type II, the N-terminal sequence V-Q-N-E-S-K (SEQ ID NO: 2) was detected.

EXAMPLE 16

Comparison of Purification Schemes with Respect to Reduction of Clostripain

Activity of clostripain was detected as described in Example 3. Collagenase type I and type II were isolated separately from several batches of culture supernatant using the procedures of Example 9 to Example 14 ("A" preparations) and according to Example 7 ("B" preparations). The preparations were compared with respect to residual clostripain activity in the preparations. The results are summarized in Table 4.

TABLE 4

Activity of clostripain in U/mg protein

| Batch no. | 1 | 2 | 3 | 4 | 5 | 6 | 7 | Ø |
|---|---|---|---|---|---|---|---|---|
| Coll. I, (A) | | | | 0.01 | 0.017 | 0.023 | 0.027 | 0.019 |
| Coll. I, (B) | | 0.04 | 0.11 | | | | | 0.075 |
| Coll. II, (A) | | | | 0.042 | 0.059 | 0.049 | 0.051 | 0.053 |
| Coll. II, (B) | 0.09 | 0.3 | 0.07 | | | | | 0.153 |

Coll. = Collagenase
Ø = average

The data further illustrate efficient removal of clostripain activity in the "A" preparations. As a result, degradation of the respective desired collagenase enzyme was significantly reduced and provided the basis for an enhanced quality of the enzyme preparations.

EXAMPLE 17

Determination of Tryptic Activity in Preparations of Collagenase Type I and Type II Preparations Activity of trypsin was detected as described in Example 4. Collagenase type I and type II were isolated separately from several batches of culture supernatant using the procedures of Example 9 to Example 14 ("A" preparations). The preparations were analyzed with respect to residual trypsin activity in the preparations. The results are summarized in Table 5.

TABLE 5

| | Activity of trypsin in U/mg protein | | | | |
|---|---|---|---|---|---|
| Batch no. | 4 | 5 | 6 | 7 | Ø |
| Coll. I, (A) | 0.00014 | 0.00015 | 0.00021 | 0.00013 | 0.00016 |
| Coll. II, (A) | 0.00053 | 0.001 | 0.00064 | 0.0004 | 0.00064 |

Coll. = Collagenase
Ø = average

The data further illustrate efficient removal of tryptic activity in the "A" preparations. As a result, degradation of the respective desired collagenase enzyme was significantly reduced and provided the basis for an enhanced quality of the enzyme preparations.

What is claimed is:

1. A method for purifying *Clostridium histolyticum* collagenase type I and type II proteins from a complex mixture comprising the steps of
    providing the complex mixture dissolved in an aqueous liquid phase,
    forming a precipitate of collagenase type I and type II proteins by dissolving ammonium sulfate in the liquid phase,
    separating the precipitate from the liquid phase,
    dissolving the separated precipitate in an aqueous buffer comprising Ca2+ ions and having a pH between 6.0 and 8.0, and adjusting the conductivity of the buffer with the dissolved precipitate to a value between 50 and 300 mS/cm, thereby forming a complex buffered solution comprising collagenase type I and type II proteins, reducing clostripain proteolytic activity by a factor of between 90 and 150 and reducing tryptic activity by a factor of between 100 and about 400 relative to the respective proteolytic activities in the complex mixture dissolved in the aqueous liquid phase,
    extracting the complex buffered solution by contacting it with a hydrophobic stationary phase and adsorbing collagenase type I and type II proteins to the stationary phase,
    separating the hydrophobic stationary phase with the adsorbed collagenase type I and type II proteins from the extracted solution, and
    eluting the collagenase type I and type II proteins from the stationary phase, thereby purifying the collagenase type I and type II proteins.

2. The method of claim 1, further comprising the step of further purifying the eluted collagenase type I and type II proteins by cation exchange chromatography, whereby further residual proteolytic activity is further separated from the collagenase type I and type II proteins.

3. The method of claim 2, wherein the type I and type II proteins obtained after cation exchange chromatography are separated by performing the steps of
    contacting the further purified collagenase type I and type II proteins with an anion exchanging stationary phase and adsorbing the collagenase type I and type II proteins to the stationary phase, and
    eluting, in separate fractions, collagenase type I and collagenase type II proteins from the stationary phase, whereby collagenase type I and collagenase type II proteins are purified separately.

4. The method of claim 3, wherein about 82% of the collagenase type I protein in the collagenase type I fraction obtained has a molecular weight of about 114 kDa.

5. The method of claim 3, wherein about 82% of the collagenase type I protein in the collagenase type I fraction obtained is N-terminally intact.

6. The method of claim 3, wherein the clostripain activity in the collagenase type I fraction obtained is less than about 0.04 U/mg of protein.

7. The method of claim 3, wherein about 93% of the collagenase type II protein in the collagenase type II fraction obtained has a molecular weight of about 112 kDa.

8. The method of claim 3, wherein about 93% of the collagenase type II protein in the collagenase type II fraction obtained is N-terminally intact.

9. The method of claim 3, wherein the clostripain activity in the collagenase type II fraction obtained is less than about 0.07 U/mg of protein.

10. The method of claim 3, wherein a first measured amount of collagenase type I protein in the collagenase type I fraction obtained and a second measured amount of collagenase type II protein are blended in a subsequent step.

11. The method of claim 3, wherein a first measured amount of collagenase type II protein in the collagenase type II fraction obtained and a second measured amount of collagenase type I protein are blended in a subsequent step.

* * * * *

SEQUENCE LISTING

```
<160> NUMBER OF SEQ ID NOS: 3

<210> SEQ ID NO 1
<211> LENGTH: 6
<212> TYPE: PRT
<213> ORGANISM: Clostridium histolyticum

<400> SEQUENCE: 1

Ile Ala Asn Thr Asn Ser
1               5

<210> SEQ ID NO 2
<211> LENGTH: 6
<212> TYPE: PRT
<213> ORGANISM: Clostridium histolyticum

<400> SEQUENCE: 2

Val Gln Asn Glu Ser Lys
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Pro Leu Gly Pro Arg
1               5
```